United States Patent
Sharrow et al.

[11] Patent Number: 5,243,679
[45] Date of Patent: Sep. 7, 1993

[54] OPTICAL FIBER ADVANCEMENT, RETRACTION AND STORAGE SYSTEM

[75] Inventors: James S. Sharrow, Bloomington; Jayne G. Fangel, White Bear Lake, both of Minn.

[73] Assignee: GV Medical, Inc., Minneapolis, Minn.

[21] Appl. No.: 832,445

[22] Filed: Feb. 7, 1992

[51] Int. Cl.⁵ .............................................. G02B 6/36
[52] U.S. Cl. ........................................ 385/135; 385/134
[58] Field of Search ............... 385/135, 134, 136, 137, 385/138

[56] References Cited

U.S. PATENT DOCUMENTS

| | | | |
|---|---|---|---|
| 4,057,186 | 11/1977 | Hedger | 226/127 |
| 4,669,465 | 6/1987 | Moore et al. | 128/303.1 |
| 4,846,343 | 7/1989 | Rupert | 385/135 X |
| 4,898,448 | 2/1990 | Cooper | 385/135 X |
| 4,900,123 | 2/1990 | Barlow et al. | 385/135 X |
| 5,067,784 | 11/1991 | Debortoli et al. | 385/135 X |

Primary Examiner—John D. Lee
Assistant Examiner—Phan T. Heartney
Attorney, Agent, or Firm—Merchant, Gould, Smith, Edell, Welter & Schmidt

[57] ABSTRACT

An optical fiber storage and manipulation system (1) is disclosed, including a storage container (2) and a fiber insertion tool (3). The storage apparatus (2) includes a housing (11) containing a reel (13) onto which portions of a bare fiber (6) as well as a sheathed tube (36) coaxially covering the fiber (6) is wound. The fiber (6) may be withdrawn from the housing (11) and inserted into a fiber insertion tool (3) having a frame (15) which houses a sliding fiber gripping assembly (16) which permits the application of longitudinal compressive force to the fiber and advances the fiber (6) by means of a fiber advance tube (17) which telescopes into a larger diameter cannula insertion tube (18). The present system can be used, for example, in the field of laser angiosurgery in which arterial blockages are removed by the application of laser energy to arterial blockages by means of advancing an optical fiber to the site of the blockage. The present system permits advancement of the fiber (6) through a relatively tortuous path without damage to the fiber.

8 Claims, 5 Drawing Sheets

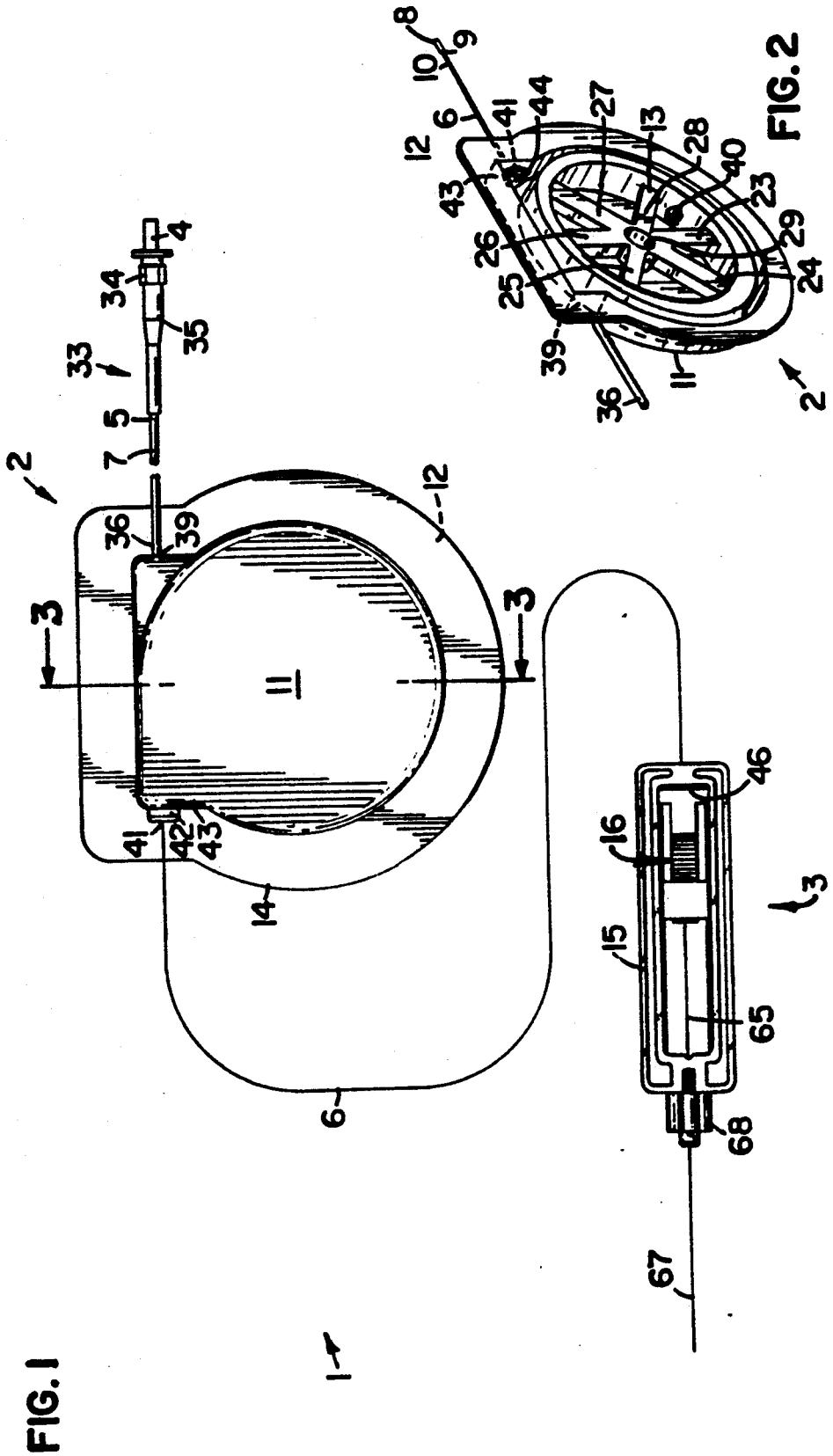

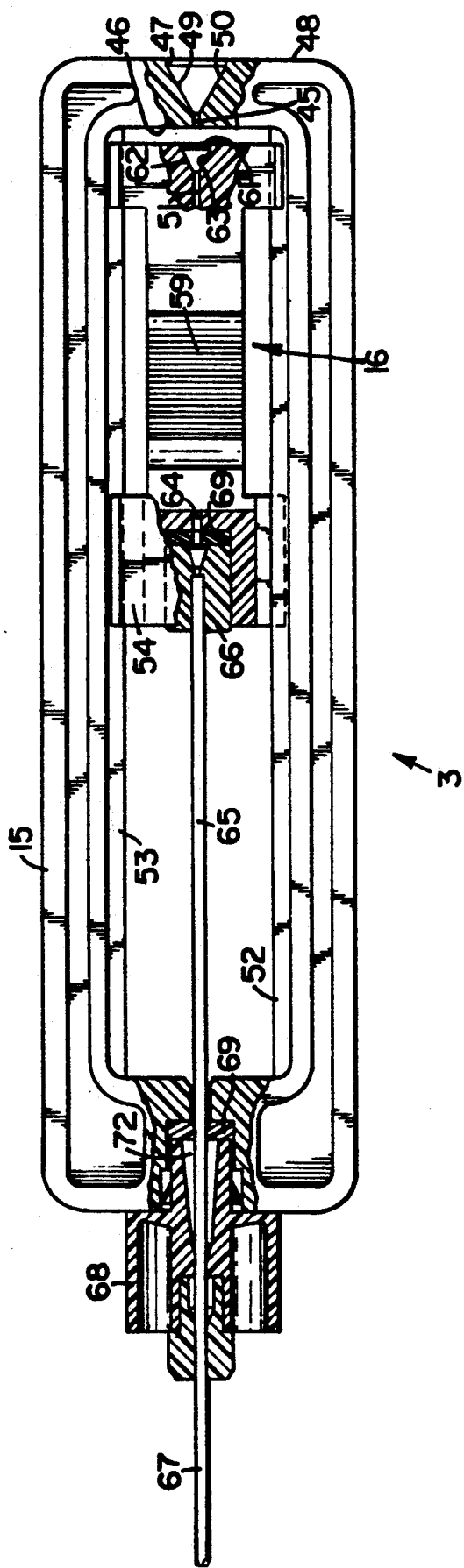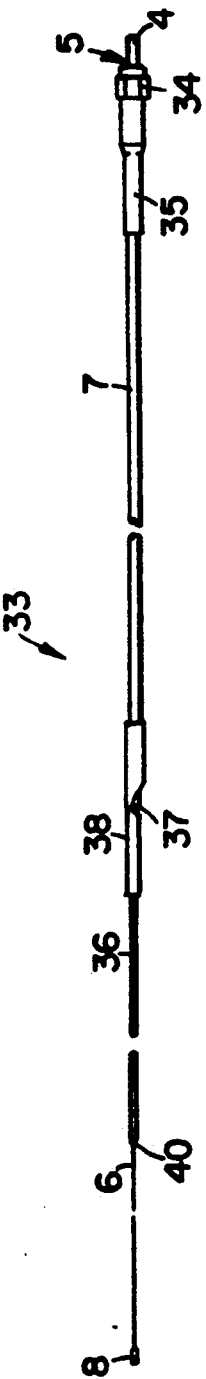

OPTICAL FIBER ADVANCEMENT, RETRACTION AND STORAGE SYSTEM

BACKGROUND OF THE INVENTION

1. Field of the Invention

The present invention relates to devices for manipulating an optical fiber. More particularly, the present invention is directed to a system for storing and dispensing a coaxially housed optical fiber and for securely gripping and longitudinally advancing the fiber when guided through a lumen having a tortuous path.

2. Description of Related Technology

Various technologies require that an optical fiber be kept in a sterile environment from which it may be withdrawn as needed. Some applications require that the optical fiber be stored again after a period of use. Also, there may be some requirement that the fiber be advanced along a path which offers some longitudinal resistance.

Although optical fibers are used in a broad variety of illumination and communication devices, a particular technology that requires all of the characteristics of sterility, reusability, controlled withdrawal of a fiber from a coaxial sheath, and advancement of the fiber along a tortuous path is the field of laser enhanced transluminal angioplasty catheters. Laser enhanced catheter devices are useful for treatment of certain types of obstructions or occlusions formed or created in blood vessels which have plaque build-up or the like, with exposure to laser beam energy being undertaken in order to obtain either a partial removal, reduction and/or the elimination of the obstruction by means of such exposure. An optical fiber member is utilized for transmitting or conducting a beam of laser energy from a generator onto an output lens for delivery of the laser energy onto or against the plaque or other matter obstructing or occluding a blood vessel. Laser enhanced transluminal angioplasty catheter devices are considered valuable tools for the treatment of commonly encountered forms of arteriosclerosis and the like.

In many cases, this procedure is effective in reopening the blood vessel and restoring substantially normal circulation. The procedure is, however, especially dependent upon the skill of the physician, and particularly as that skill pertains to manipulation and ultimate direction and control of the catheter.

Previous devices having broad application to the advancement of wires or extremely slender cylindrical members are disclosed, for example, in U.S. Pat. No. 4,057,186, which discloses a wiring pen for use in advancing a relatively rigid copper wire. Such a device is unsuitable for use with an optical fiber due to the extreme flexibility and poor longitudinal compressive resistance of the optical fiber member.

A system designed to manipulate an optical fiber in the context of laser enhanced transluminal angioplasty catheters is disclosed, for example, in U.S. Pat. No. 4,669,465, which includes a hand-held fiber advance unit which controls the insertion or extent of advance of the lasing fiber relative to the distal tip of the catheter. This particular device suffers from mechanical complexity and a lack of tactile feedback to the operator who is necessarily required to make extremely subtle adjustments regarding the absolute position of the optical fiber.

SUMMARY OF THE INVENTION

The present invention is intended to simplify the mechanical problems related to the storage and manipulation of an optical fiber.

In particular, the present invention includes a reel upon which a coaxially sheathed optical fiber is stored, and which permits the optical fiber to be easily withdrawn from the reel or retracted onto the reel simply by pulling in the appropriate direction. The reel/spool combination greatly simplifies the problem of handling and storing the optical fiber during the performance of an actual medical procedure. The thin and transparent nature of the fiber makes it otherwise difficult to perceive in the low ambient light conditions of a catheter laboratory, making it susceptible to falling on a floor, or otherwise leaving the sterile field.

A fiber insertion tool then accepts the exposed optical fiber, and enables the operator to forcibly and controllably advance the relatively flexible and non-rigid fiber along a relatively tortuous path. The fibers have a high compressive strength but are extremely brittle if compression is not kept axial, then fracture can easily occur due to the compressive force on one side of the longitudinal axis and the tensile force on the opposite side of the longitudinal axis. The fiber insertion tool dramatically reduces buckling of the fiber during the application of a longitudinal, compressive force and assists the user in applying force in the desired direction.

BRIEF DESCRIPTION OF THE DRAWINGS

An embodiment of the invention is shown, by way of example, in the accompanying Drawings, in which:

FIG. 1 is an elevational view of a fiber manipulation system built in accordance with the principles of the present invention;

FIG. 2 is a perspective view of a fiber storage spool constructed in accordance with the principles of the present invention;

FIG. 5 is a side elevation, with some internal structure partially revealed, of the fiber insertion implement depicted in FIG. 1;

FIG. 11 is a side elevation of an optical fiber cable assembly as utilized in the fiber manipulation system depicted in FIG. 1.

DESCRIPTION OF THE PREFERRED EMBODIMENT

Figure 3:
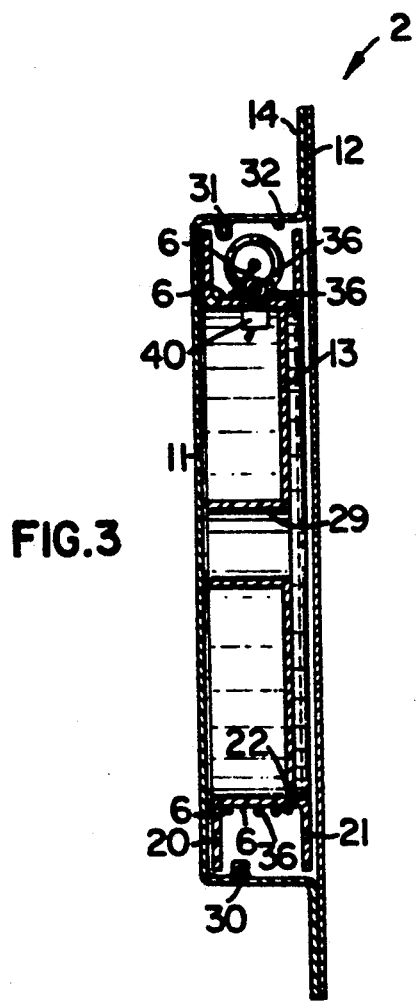
FIG. 3 is a cross-sectional view taken along lines 3—3 of FIG. 1.

Referring to FIG. 1, a fiber storage, advancement, retrieval and manipulation system is shown generally at 1. This system 1 includes a fiber storage assembly shown generally at 2 and a fiber insertion accessory or implement shown generally at 3.

In general terms, the system 1 begins with an optical connector 5, protected by a dust cap 4, which is connected to the proximal end of a coated optical fiber 6 which resides coaxially within tube or sheath 7.

In a preferred embodiment, the sheath 7 is formed of a polyethylene material, having a smooth inside surface of approximately 0.02 inches inside diameter. While the physical properties described herein are not pertinent to the broader design, the specifications set forth have been used in a successful commercial embodiment of the invention. A typical specification for the sheath 7 is that it should be capable of supporting a tensile load of 2,560 lbs., and the total elongation should be no greater than approximately 125% under this load.

The coated optical fiber 6 is typically a 200 micrometer core diameter quartz optical fiber which has a lubricated external surface to facilitate passage through conduits, sheaths, lumens or other orifices. The distal tip 10 may be fitted with an optical assembly featuring a sapphire lens 8 and radiodense tube 9 adapted to deliver laser energy having a particular pattern or flux density. Ideally, the optical assembly would tend to diverge emitted laser light and provide a feedback mechanism that monitors fiber integrity. Adjacent to the optical assembly is a radiodense fiber tip marker 9 which permits fluoroscopic visualization of the distal end 10 of the optical fiber 6.

Referring to FIGS. 1 and 2, the spool or optical fiber storage housing 2 is formed as a tray 11 sealed by a lid 12. In FIG. 2, the lid 12 has been removed to permit viewing of reel 13.

The lid 12 is typically of a flexible, sheet-like material formed of a material such as "TYVEK," styrene, or the like. The tray 11 is formed of a more rigid material such as "PET-G,"as well as styrene, both the tray 11 and lid 12 being shaped so as to have a peripheral flange 14. In use, the flange 14 is used for clamping or otherwise securing spool assembly or housing 2 to a solid or fabric surface (not shown) or to facilitate gripping by hand during manual operation.

Figure 4:
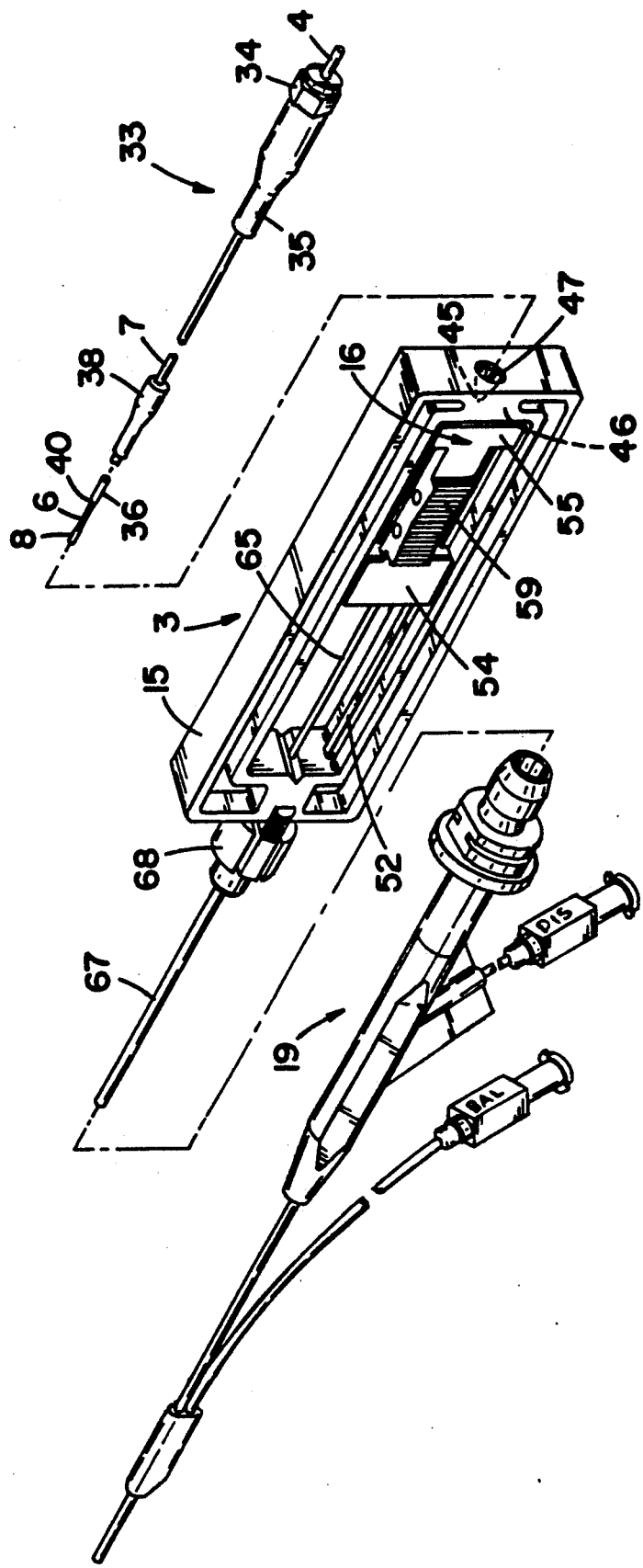
FIG. 4 is a perspective view of a fiber insertion implement as depicted in FIG. 1, including the catheter handle.
Figure 6:
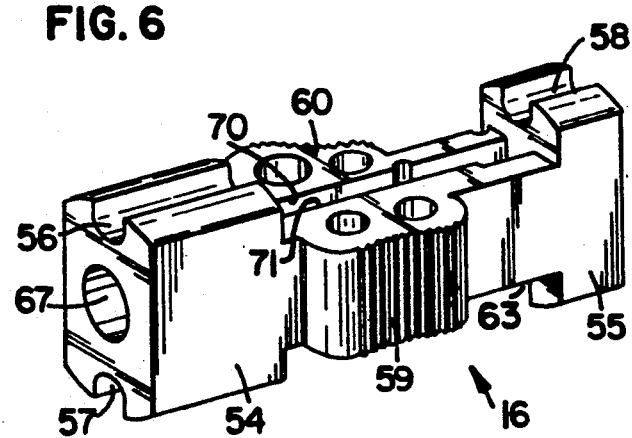
FIG. 6 is a perspective view of a fiber gripping element which is a part of the fiber insertion implement depicted in FIG. 1.
Figure 7:
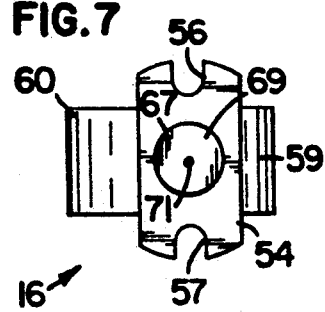
FIG. 7 is a front elevation of the fiber gripping element as depicted in FIG. 6.
Figure 8:
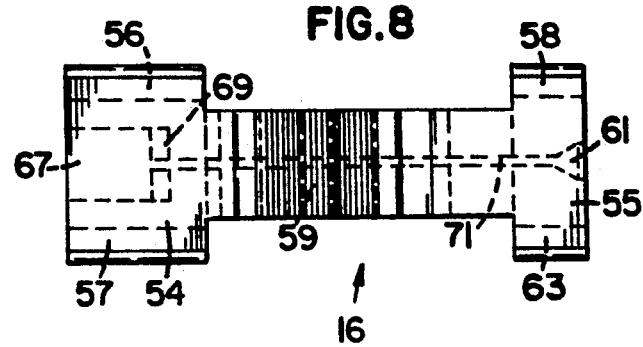
FIG. 8 is a size elevation of the gripping element as depicted in FIG. 6.
Figure 9:
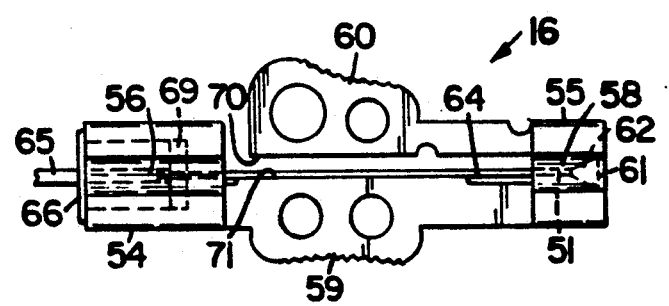
FIG. 9 a plan view of the gripping element as depicted in FIG 6, shown in the "open" position.

Shown generally at 3 is the second component of the fiber insertion system, which includes a frame 15 which is designed to be gripped by the hand (not shown) of a user of the device 3. The fiber 6 enters the frame and passes through gripping element 16 and is sheathed in a stainless steel tube 65. Tube 65 has an outside diameter slightly smaller than the inside diameter of insertion cannula 67 which is designed to fit into a catheter handle 19 such as shown in FIG. 4.

Referring to FIGS. 2 and 3, the structure and operation of the spool or housing 2 can be understood. The housing 2 contains a reel 13 which, in a preferred embodiment, is composed of medium impact styrene. The outer flanges 20 and 21 have an outside diameter of approximately 3½ inches while the inner hub 22 has a diameter of approximately 2.85 inches. The area between the flanges 20 and 21 and bounded by the surface of inner hub 22 defines a channel within which, for example, a fiber may be wound and stored. The height of the hub 22, that is, the distance between flanges 20 and 21, is approximately 0.656 inches. The reel 13 is formed to have a series of spokes 23, 24, 25, 26, 27 and 28, all converging about a central orifice 29. Although the central orifice 29 could be used for support of the reel upon a shaft, in a preferred embodiment the reel is supported inside the housing 11 by means of peripherally located reel restraining lips or protrusions 30 and 31 which are formed integrally upon inner wall 32 of housing 11. The lips 30 and 31 are conveniently spaced about flange 20 to provide some restraint on the lateral movement of the reel 13 while permitting reel 13 to freely rotate within housing 11. Residing within the region defined between flanges 20 and 21 and radially outward of reel 22 is a major portion of optical cable 33, best seen in FIG. 11. In a preferred embodiment, the cable is approximately 197 centimeters in length from the tip of optical assembly 8 to the opposite tip of optical connector 5. The optical connector itself is threadably attached by means of nut 34 to a suitable mating connector (not shown) of a laser energy source (not shown). The connector is bonded to fiber optic cable 7, the interface being sealed by heat shrinkable tubing 35.

Housed within the fiber optic cable 33 is a length of sheathed tubing 36.

In a preferred embodiment, the length of the sheathed tubing 36 is approximately 300 centimeters. However, only approximately 78 centimeters actually reside within the thicker fiber optic cable 7, with approximately 40 centimeters being exposed or unshielded without the protective covering of the fiber optic cable 7. The junction 37 between fiber optic cable 7 and sheathed tubing 36 is protected by heat shrinkable tubing section 38. Finally, residing coaxially within the sheathed tubing 36 for its entire length or, for example, 118 centimeters, is a polished optical fiber 6, which extends beyond the sheathed tubing 36 for an additional distance of approximately 150 centimeters. Only a portion of the sheathed tubing 36 and the polished fiber 6 in the region between optical assembly 8 and heat shrinkable tubing 38 actually resides on reel 13 within housing 11.

As sheathed tubing 36 enters opening 39 of housing 11, the sheathed tubing 36 is wrapped circumferentially within the channel residing around the outer surface of hub wall 22, the sheathed tubing being secured or anchored in place at a single point along the hub wall by some suitable fiber securing device such as fastener 40. As sheathed tubing 36 continues along the path around the reel 13 perimeter, the sheathed tubing 36 eventually ends at a point just distal to section 38. The unsheathed polished fiber 6 continues to be wound around reel 13 and eventually exits through orifice 41. In a preferred embodiment, orifice 41 has a diameter only slightly greater than the outside diameter of the fiber 6, the orifice 41 being formed within a silicone button or grommet 42 which is press-fit into the wall 43 of housing 11. The rear portion 44 is typically formed to have inwardly tapered walls, much like a funnel, to serve as a guide for inserting the fiber 6 and optical assembly 10 through orifice 41 during assembly.

When finally assembled, a relatively large length of sheathed tubing 36 extends outwardly from orifice 39, while only a short length of fiber 6 extends outwardly from housing 11 through orifice 41. In operation, in order to unwind the fiber 6 from storage housing 2, one need only grasp the polished fiber 6 and pull the polished fiber 6 from the housing 11 until an adequate length of fiber 6 is exposed for use. In order to rewind fiber 6 into assembly 2, one need only pull on sheathed tubing 36 which will cause the reel 13 to rotate in the opposite direction, thereby rewinding fiber 6 onto reel 13.

Referring now to FIGS. 4-10, the construction and operation of the fiber insertion tool 3 will be described.

The fiber 6 is inserted through frame 15 so as to pass initially through orifice 45 located in the inner side wall 46 of frame 15. As seen in FIG. 5, an opening 47 is formed with an outer rear wall 48 of frame 15, the opening 47 having a diameter substantially larger than that of orifice 45 and being formed so as to have tapered wall 49 so as to assist in the guidance of fiber 6 through orifice 45.

Figure 10:
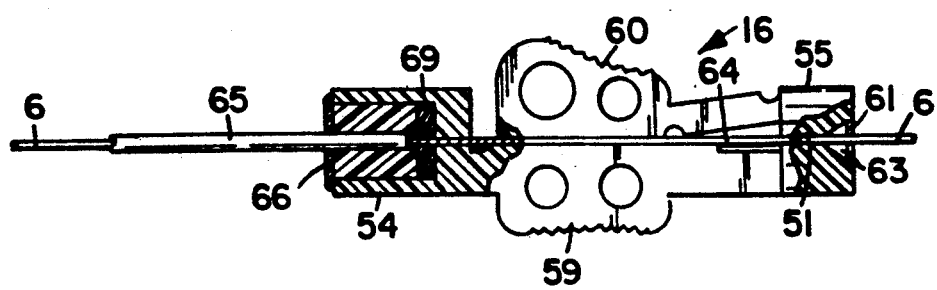
FIG. 10 is a plan view of the gripping element as shown in FIG. 6, shown in the "closed" position.

Longitudinally aligned with orifice 45 is rearward slide orifice 51 which is a part of slide assembly 16. Slide assembly 16 is longitudinally slidable within frame 15 along rails 52 and 53 which are formed integrally along the longitudinal inner side walls of frame 15. The slide assembly 16 is formed so as to have a forward section 54 and a rearward section 55. Grooves 56 and 57 mate with rails 53 and 52, respectively, while groove 58 is slidably engaged with rail 53 of frame 15. Formed integrally with and residing between forward section 54 and rear section 55 is left tab 59 and right tab 60. The surfaces of tabs 59 and 60 are roughened or knurled in order to facilitate gripping engagement by human fingers. The slide assembly is shown in its normal, open configuration in FIG. 9. Opening 51 receives fiber 6 (not shown) through tapered orifice 61 which is formed so as to have sloping walls 62 and 63 which serve to guide optical fiber 6 through the relatively narrow confines of orifice 51. Orifice 51 leads to and connects with resilient tube 64, tube 64 passing between tabs 59 and 60 and being engageable thereby when tabs 59 and 60 are depressed as shown in FIG. 10. Tube 64 is joined to fiber advance tube 65 at junction 66. In a preferred embodiment, fiber advance tube 65 is composed of stainless steel and has a diameter of approximately 0.032 inches. Fiber advance tube 65 is bonded to seal cap 66 and passes through seal 69 which is housed within cavity 72 of forward section 73.

The fiber advance tube 65 is longitudinally aligned with cannula insertion tube 67, which is of a slightly larger diameter than fiber advance tube 65, thereby allowing fiber advance tube 65 to telescope within tube 67. A keyed connector 68 is affixed to the forward end of frame 15 to permit rigid attachment of the fiber insertion tool to a catheter housing 19. A seal 69 is provided at the junction of tube 65 and 67 to prevent seepage of fluids which might be introduced through the catheter housing 19.

In operation, the fiber 6 may be inserted through orifices 47, 45, 61, 51, through tube 64, 65, and completely through the length of tube 67 and into a suitable catheter housing. Normally, such fiber insertion can be performed by hand since the resistance encountered is usually minimal. However, in some instances, the fiber is required to follow a tortuous path in order to reach the site where laser energy will be applied by the optical assembly 8. In such cases, an additional compressive force must be applied longitudinally along the fiber 6 without damaging the fiber or causing it to buckle. As seen in FIG. 10, if resistance is encountered, tabs 59 and 60 may be depressed, causing inner surface 70 of tab 60 to engage tube 64, thereby pressing tube 64 against inner wall 71 of tab 59. Ideally, the tube 64 is constructed of a material such that the wall cannot be compressed to an extent that would cause damage to the optical fiber 6 housed within even with a large force applied by tabs 59 and 60.

During the initial attempt to advance fiber 6 along a tortuous path, the slide assembly 16 is in the rearward position shown in FIG. 5. When additional longitudinal compressive force is needed, tabs 59 and 60 are depressed and the entire assembly 16 slides forwardly along rails 52 and 53 causing fiber advance tube 65 to move forward and telescope within cannula insertion tube 67. In this way, fiber 6 is advanced a distance equal to the length of travel of the slide 16 along rails 52 and 53. When maximum forward travel of the slide 16 has been reached, tabs 59 and 60 may be released and the assembly 16 may be translated rearwardly in order that the process may be repeated as often as necessary.

Other embodiments of the invention will be obvious to those skilled in the art. Thus, change in shape of either the frame, the tabs, or the slide assembly are changes of form, not substance, and do not affect the advance of the fiber according to the method of the invention. Such changes are within the scope of the claims which follow.

We claim:
1. A fiber manipulation device, comprising:
    (a) a frame, the frame having a longitudinal axis;
    (b) at least one rail, the rail being affixed to the frame, the rail being substantially parallel to the longitudinal axis; and
    (c) gripping means adapted to engage the rail and slidable advance thereon, the gripping means for releasably securing a fiber, thereby permitting the fiber to be translated parallel to the longitudinal axis, the gripping means further comprising:
        (1) a further section;
        (2) a rearward section;
        (3) a first tab, the first tab residing between and being rigidly attached to the forward section and the rearward section; and
        (4) a second tab, the second tab residing opposite to the first tab and between the forward section and the rearward section, thereby permitting the second tab to be displaced towards the first tab so as to exert a shear force on an object therebetween.

2. The fiber manipulation device of claim 1, further comprising a resilient tube, the resilient tube residing between the first tab and the second tab such that the resilient tube may be deformed by displacing the second tab toward the first tab.

3. The fiber manipulation device of claim 2, further comprising:
    (a) a fiber inlet orifice, the fiber inlet orifice being formed within the frame, the fiber inlet orifice being coaxially aligned with the resilient tube; and
    (b) a fiber advance tube, the fiber advance tube being coaxially aligned with the resilient tube, the fiber advance tube being rigidly affixed to the forward section of the gripping means.

4. The fiber manipulation device of claim 3, further comprising a cannula, the cannula being coaxially aligned with the fiber advance tube, the cannula being rigidly affixed to the frame in a region opposite to the fiber inlet orifice.

5. The fiber manipulation device of claim 4, wherein the fiber advance tube has a first diameter, the cannula has a second diameter, the second diameter is greater than the first diameter, thereby permitting the fiber advance tube to telescope into the cannula as the gripping means is advanced within the frame.

6. The fiber manipulation device of claim 5, wherein the fiber inlet orifice has an entrance diameter and an outlet diameter, the entrance diameter being greater than the outlet diameter, the fiber inlet orifice having tapered walls transitioning between the entrance and the outlet, thereby serving as a guide for a fiber inserted into the fiber inlet orifice.

7. The fiber manipulation device of claim 6, further comprising a keyed connector, the keyed connector being rigidly affixed to the frame, the keyed connector being rigidly affixed to a portion of the cannula and being coaxial therewith, thereby permitting the fiber manipulation device to be releasably affixed to a catheter housing.

8. A method of storing and manipulating a fiber, comprising the steps of:
   (a) winding a partially sheathed fiber onto a reel;
   (b) mounting the reel within a housing;
   (c) forming a flange around at least a portion of the housing to facilitate anchoring the housing during use;
   (d) forming a first and second exit orifice within the housing;
   (e) beveling the second exit orifice in order to facilitate guidance of the unsheathed fiber through the orifice;
   (f) aligning a sheathed portion of the fiber with the first exit orifice; and
   (g) aligning an unsheathed portion of the fiber with the second exit orifice such that withdrawing the sheathed portion of the fiber from the housing causes the unsheathed portion of the fiber to be rewound onto the reel;
   (h) forming a frame having longitudinally aligned rails;
   (i) forming a fiber inlet orifice within the frame;
   (j) mounting a fiber gripper within the frame so as to be slidable along the rails;
   (k) inserting an unsheathed fiber withdrawn from the second exit orifice through the fiber inlet orifice;
   (l) gripping the unsheathed fiber with the fiber gripper; and
   (m) slidably advancing the fiber griper within the frame so as to advance the fiber.

* * * * *

UNITED STATES PATENT AND TRADEMARK OFFICE
CERTIFICATE OF CORRECTION

PATENT NO. : 5,243,679

DATED : September 7, 1993

INVENTOR(S) : JAMES S. SHARROW and JAYNE G. FANGEL

It is certified that error appears in the above-identified patent and that said Letters Patent is hereby corrected as shown below:

```
In column 2, line 56, after "9" insert --is--.
In column 6, line 25, for "slidable" read --slidably--.
In column 6, line 29, for "further" read --forward--.
In column 8, line 20, for "griper" read --gripper--.
```

Signed and Sealed this

Twelfth Day of April, 1994

Attest:

BRUCE LEHMAN

*Attesting Officer*     *Commissioner of Patents and Trademarks*